(12) United States Patent
Genet et al.

(10) Patent No.: US 8,300,326 B2
(45) Date of Patent: Oct. 30, 2012

(54) MINIATURIZED OPTICAL HEAD WITH HIGH SPATIAL RESOLUTION AND HIGH SENSITIVITY, ESPECIALLY FOR FIBRED CONFOCAL FLUORESCENCE IMAGING

(75) Inventors: Magalie Genet, Guyancourt (FR); Gilles Mathieu, Lunel (FR); Bertrand Viellerobe, Nogent sur Marne (FR); François Doussoux, Paris (FR); Nicolas Boularot, Champigny sur Marne (FR); Nicolas Lavillonniere, Saint Maur des Fosses (FR)

(73) Assignee: Mauna Kea Technologies, Paris (FR)

( * ) Notice: Subject to any disclaimer, the term of this patent is extended or adjusted under 35 U.S.C. 154(b) by 381 days.

(21) Appl. No.: 12/299,158

(22) PCT Filed: Apr. 27, 2007

(86) PCT No.: PCT/FR2007/000723
§ 371 (c)(1),
(2), (4) Date: Jul. 30, 2010

(87) PCT Pub. No.: WO2007/128909
PCT Pub. Date: Nov. 15, 2007

(65) Prior Publication Data
US 2010/0296178 A1    Nov. 25, 2010

(30) Foreign Application Priority Data

May 5, 2006   (FR) ..................................... 06 04019

(51) Int. Cl.
*G02B 9/34*   (2006.01)
(52) U.S. Cl. ........................................ 359/771; 359/754
(58) Field of Classification Search .......... 359/754–795; 385/33, 119
See application file for complete search history.

(56) References Cited

U.S. PATENT DOCUMENTS

| | | | |
|---|---|---|---|
| 3,700,311 A | 10/1972 | Shoemaker | |
| 5,469,299 A | 11/1995 | Nagano | |
| 7,215,478 B1 * | 5/2007 | Hirata | 359/656 |
| 7,215,479 B1 * | 5/2007 | Bakin | 359/664 |

(Continued)

FOREIGN PATENT DOCUMENTS

JP    93 29748 A    12/1997

(Continued)

OTHER PUBLICATIONS

International Search Report and French Search Report, Aug. 2007.

(Continued)

*Primary Examiner* — Darryl J Collins
(74) *Attorney, Agent, or Firm* — Young & Thompson

(57) ABSTRACT

A miniaturized optical head provided to equip the distal end of a beam of flexible optical fibers scanned by a laser beam, is designed to come in contact with a sample and to excite the sample confocally. This optical head includes elements for correcting spherical aberrations and focusing members. The focusing members include: at least a first lens (L4) of high convergence associated with a spherical or hemispherical lens (L5) arranged at the distal end of the optical head, and elements for correcting the axial and lateral chromatic aberration provided with a single divergent lens (3b) whose curvature is substantially centered on the pupil of the optical fiber beam and arranged at the exact distance for this pupil for which the conditions of lateral achromatization coincide with the conditions of axial achromatization; this divergent lens being associated with a second convergent lens (L3a) in the form of a doublet (L3).

17 Claims, 1 Drawing Sheet

U.S. PATENT DOCUMENTS

| | | |
|---|---|---|
| 7,221,824 B2 | 5/2007 | Berier et al. |
| 2004/0252380 A1 | 12/2004 | Kashima |
| 2006/0007558 A1 | 1/2006 | Hirata |

FOREIGN PATENT DOCUMENTS

| | | |
|---|---|---|
| JP | 10 090113 A | 4/1998 |
| JP | 2004313769 A | 11/2004 |
| JP | 2005512747 A | 5/2005 |
| JP | 2006023389 A | 1/2006 |
| WO | 03056379 | 7/2003 |
| WO | 2004065994 | 8/2004 |

OTHER PUBLICATIONS

Andrew R. Rouse et al., "Design and demonstration of a miniature catheter for a confocal microendoscope", Applied Optics, Nov. 2004, V43, No. 31, pp. 5763-5771.

* cited by examiner

MINIATURIZED OPTICAL HEAD WITH HIGH SPATIAL RESOLUTION AND HIGH SENSITIVITY, ESPECIALLY FOR FIBRED CONFOCAL FLUORESCENCE IMAGING

The present invention relates to a miniaturized optical head provided to equip a distal end of a bundle of flexible optical fibres, said head being intended to be placed in contact with an analysis surface and adapted to focus an excitation signal conveyed by said fibre bundle into an excitation focal point that can be situated at different depths relative to the contact surface of the head. The optical head is also adapted to sample a back-emitted signal originating from the sub-surface excitation focal point in order that it is directed by the fibre bundle in particular to detection means and means for analysis and digital processing of the signal.

BACKGROUND OF THE INVENTION

The fields of application concerned are sub-surface analysis devices of confocal character, the conveyed signals being able to be in particular in the field of imaging and/or the spectroscopy depending on the excitation source(s) and the detection means used. The confocal character results from the use of the same fibre to convey the excitation signal and the back-emitted signal, and a very reduced spatial dimension of the fibre. These may be in-situ biological analyses, on people or animals, external for example in the field of dermatology, or internal and accessible with the help of an endoscope operating channel into which the bundle of optical fibres and the optical head can be introduced. They may also be cell analyses carried out ex vivo on samples. Furthermore, the optical head can also be used for the analysis of the interior of a manufactured device.

The medical fields concerned in the present case are gastroenterology, pneumology, gynaecology, urology, ORL, dermatology, opthalmology, cardiology and neurology.

The means of signal analysis and processing provided on the proximal end side of the bundle of optical fibres allow the restoration of an image or a graph that can be interpreted by a user.

Document WO 03/056379 is known, describing a miniaturized optical head envisaged for equipping the distal end of an image guide. This optical head consists of an optics-holder tube of circular section within which are introduced, on one side, the distal terminal part of the image guide and, on the other, optical focusing means. The optical means comprise lenses arranged in extra-focal planes. The lenses are arranged so as to optimize the signal-to-noise ratio by minimizing the stray reflection at the output of the image guide, by optimizing the return coupling level and by optimizing the transmission of the head assembly. The subject of the present invention is an optical head offering a good image quality for fluorescence systems in particular.

The document by A. R. Rouse, A. Kano, J. A. Udovich, S. M. Kroto and A. F. Gmitro, "Design and demonstration of a miniature catheter for a confocal microendoscope", Applied Optics, vol. 43, no 31, pp. 5763-5771, 2004, is also known. This document describes an optical head which is located in the distal part of an image guide. This optical head has the following characteristics:
- Magnification=1.6, which makes very little difference and does not allow a large lateral resolution to be obtained;
- Numerical aperture on the tissue=0.46, which is a drawback for the collection of the photons from the fluorescence of the tissue; the sensitivity cannot be very high with such an optical solution;
- Diameter of the head=3 mm;
- Length of the head=13 mm, which is compatible with the passage through the operating channel of an endoscope;
- Point axial resolution=10 µm, which is a fairly large value for an optical head comprising a relatively complicated optical design;
- Planar axial resolution=25 µm (i.e. for an entire image field), which is a significant value for an optical head comprising a complicated optical design;
- Lateral resolution=3 µm, fairly degraded for an optical head of this type.

The optical head according to the prior art does not have optical performance values that allow it to be ranked as an optical head with high resolution and high sensitivity. Moreover, the Rouse document describes a direct line-by-line scanning system and not a point-by-point scanning system injecting the optical beam in turn into each of the optical fibres constituting the image guide.

SUMMARY OF THE INVENTION

The purpose of the present invention is to remedy the drawbacks of the optical head of the prior art by proposing a miniature optical head of high optical quality: high resolution (lateral resolution and axial resolution) and high sensitivity, in particular for fibred confocal fluorescence imaging with laser scanning in vivo. The miniaturization must allow in particular the insertion of the assembly comprising image guide (bundle of optical fibres) and optical head into the operating channel of an endoscope or must be the least invasive possible in a small animal. The need for a high optical quality is part of the desire to detect small objects (membranes, dendrites, organellae, etc.) with a very good resolution and with a very good sensitivity. Thus, it would be possible to detect more easily objects situated deeper in the tissue.

Another purpose of the invention is a high-quality head particularly adapted for real-time acquisitions.

At least one of the aforementioned objectives is achieved with a miniaturized optical head envisaged to equip the distal end of a bundle of flexible optical fibres scanned by a laser beam, said optical head being intended to come into contact with a sample and excite said sample in a confocal manner; this optical head comprising means for correcting spherical aberrations and focusing means. According to the invention, the focusing means comprise:
- at least a first strongly convergent lens combined with a spherical or hemispherical lens arranged at the distal end of the optical head, and
- means for correcting axial and lateral chromatism that are provided with a single divergent lens the curvature of which is substantially centred on the pupil of the bundle of optical fibres and arranged at the correct distance from this pupil for which the lateral achromatization conditions coincide with the axial achromatization conditions; this divergent lens being combined with a second convergent lens in the form of a doublet. These conditions are such that an optimum compromise between axial and lateral aberrations is determined.

More precisely, the means for correcting spherical aberrations also correct coma and astigmatism aberrations.

Advantageously, the bundle of optical fibres is scanned by the laser beam in real time so as acquire at least twelve images per second.

With the optical head according to the invention, performances for quality of wavefront and imaging with a large numerical aperture, preferably greater than 0.8, are obtained without the need to add corrective menisci: a single divergent lens thus arranged allows very good performances to be achieved. Generally, a numerical aperture can be considered large from a value of 0.6 upwards. A large image numerical aperture allows a high sensitivity to be obtained. It allows, firstly, focusing of the excitation beam from the illumination fibre in a very confined excitation volume, which allows the maximizing of the energy density at the focal point and thus optimum excitation of the sample or tissue. For example, it also allows maximization of the collection of the number of fluorescence photons which are emitted isotropically in the sample. A numerical aperture greater than 0.8 can be obtained by using a lens or of a group of convergent lenses presenting very small radii of curvature such as for example a group of strongly convergent lenses ending in a spherical or hemispherical lens. The hemispherical lens has the advantage that it can be made with very small diameters, and ensures a good contact with the sample in order to minimize the movement inherent in the operator or in the analysed subject and carries out a good index adaptation so as to be free of the signal from the analysis surface.

Moreover, the optical head according to the invention presents a strong magnification. The magnification of the optical head is calculated as the relationship between:

the numerical aperture of the first optical block serving to correct aberrations, one of the functions of which is to adapt the numerical aperture of the optical fibres; its value is comprised between 0.3 and 0.32; and the numerical aperture (>0.8) of the second focusing optical block, tissue side, the principal function of which is to focus the beam in the tissue.

Thus, the magnification values in the present case are comprised between 2.5 and 4. This allows a much better spatial resolution to be achieved than with the other optical heads used in the prior art. This major advantage affecting the resolution is effective where the optical head is not optically aberrant.

More precisely, the means for correcting spherical aberrations include a third convergent lens; the thicknesses of the first and third convergent lenses being determined so as to correct the cumulative spherical aberration on the convergent diopters of said convergent lenses of the optical head.

Advantageously, the thickness of the third convergent lens is also determined so as to image the pupil on the second convergent lens, to minimize the aberrations.

According to an embodiment of the invention, the thickness, the radius of curvature (or optical power) and the nature of this third lens (L2) are adapted so as to image the pupil in a plane situated as close as possible to said bundle of optical fibres. Imaging the pupil as closely as possible to the output of the fibres allows a small-sized image on the pupillary plane, therefore a small diameter of the optical head, which is on the way to an optimized miniaturization.

Preferably, the glass of the third lens is determined with a small enough constringence to minimize the necessary chromatic correction power, and with a high enough refractive index to limit the spherical and coma aberration effect. Glasses of the "FLINT" type can be used for example.

According to an advantageous characteristic of the invention, said doublet is placed in a pupillary plane giving characteristics of small aberrations, in particular small astigmatism. Advantageously, a sufficient thickness of the second convergent lens is determined in order to keep the divergent lens the right distance away from the pupil for which the lateral achromatization conditions coincide with the axial achromatization conditions. Moreover, the camber or curvature of the divergent lens is centred on the pupil so as to minimize the astigmatism at the output of the divergent lens; the pupil being a surface (not necessarily plane) common to the beams leaving all points of the field. Generally, still from the point of view in the direction of propagation of the light: upon excitation, the light has left the fibres. The field is therefore the beam itself. The points of the field are then the fibres themselves. However, from the point of view of collection, on return from the sample, the field is the observed field.

Moreover, the doublet comprises a pair of lenses with a small index difference but a large chromatic dispersion difference so as to compensate the chromatic aberrations of the convergent lenses. The choice of the glasses in the doublet can be a pair of glasses with a small index deviation in order to minimize the geometric aberration terms induced in the interface between the two lenses of the doublet, but with a strong chromatic dispersion difference. The doublet thus obtained is over-corrected by the axial chromatism in order to compensate for the chromatic aberrations of the convergent elements. By way of example, the following combination of glasses can be used: lens 1 (LAK21, nd=1.6405, Vd=60.1) and lens 2 (SF6, nd=1.8052, Vd=25.4), which has a small index difference, and a large constringence difference.

The first and third convergent lenses can each be obtained from a lens having a small radius and a large radius, said large radius being made plane so as to obtain a plano-convex lens.

According to the invention, the first convergent lens is designed and arranged so as to eliminate the image of the pupil sufficiently far ahead to minimize the astigmatism generated by the spherical or hemispherical lens in the imaged field.

The optical quality of the head according to the invention is a parameter that allows an image with high spatial resolution to be obtained. This image quality is very close to the diffraction limit. The WFE (wave front error) is of the order of $\lambda/15$ at the centre of the field and $\lambda/10$ at the edge of the field. These WFE values make it possible to avoid from the presence of too-significant optical aberrations which could degrade:

1. the lateral resolution which is evaluated by the circled energy. By definition, to resolve a spot of diameter $\phi$, 50% of the energy as a minimum must be contained in this diameter. For a highly resolved probe, 50% of the energy must be contained in a diameter in the micron range. In this case, it is not the optical head which limits the lateral resolution, but the distance between the cores of the fibres constituting the image guide. The lateral resolution is given by the inter-core distance divided by the magnification of the optical head, i.e. a lateral optical resolution of less than 1.5 µm for probes used according to the present invention, which is much better than the systems of the prior art.

2. the axial resolution which is a function of the image numerical aperture, and which can be degraded by the appearance of spherical aberration. In order to ensure for example a highly resolved confocal fluorescence image, the axial resolution is preferably less than 5 µm. Given that obtaining a high sensitivity involves the use of a large numerical aperture and therefore of convergent lenses with small radii of curvature described with significant field angles which induce aberrations, obtaining a very good resolution, be it lateral or axial, involves the use of an upstream optical set (situated between the image guide and the focusing optical set) constituted by corrective lenses allowing the correction of aberrations such as coma and astigmatism which degrade the lateral resolution, and spherical aberration which degrades the axial resolution.

According to the invention, the hemispherical lens can be produced in a ball, the plane output face of which is obtained by abrasion on a plane polisher.

The thickness of the hemispherical lens can be adjusted in order to obtain a predetermined frontal area of the optical head. Moreover, the axial position of the hemispherical lens, that is to say the thickness of air between the lens which precedes it (first convergent lens) and the hemispherical lens, is determined according to the thickness of said hemispherical lens (L5) in order to optimize the optical performances (axial and lateral resolutions etc.) of the optical head, for said frontal area.

Advantageously, the optical head according to the invention also comprises a plate with plane faces for eliminating the stray reflection occurring at the output of the bundle of optical fibres.

According to the invention, the signal collected by the optical head that originates from the sample can be a fluorescence signal or a reflectance signal. In order to obtain an image in fluorescence mode, the optical head is achromatic in a spectral band between 450 nm and 800 nm. Such an achromaticity over a broad spectral band also allows use in spectroscopy and in multi-marking. This optical head is therefore also compatible with a use in reflectance imaging, since the latter operates in the near infrared covered by the broad working spectral band of the optical head.

Regarding the sampling of the tissue, the optical head according to the invention allows a good point spread function (PSF) or focal spot, in the micron range to be obtained. Moreover, the optical magnification is such that the image resolution is better than that for standard probes. Such a sampling according to the invention allows images with a better resolution to be obtained.

The optical head according to the invention allows the following performance values in particular to be achieved:

a laser scanning with rapid acquisition in real time of several images per second at least 12 images per second;

an adequate miniaturization: diameter comprised between 2 and 4.5 mm and a head length comprised between 10 and 27 mm;

a confocal head with a very good axial (<5 µm) and lateral (<1.5 µm) resolution;

a high sensitivity for collection of fluorescence photons with a tissue-side numerical aperture >0.8.

The present invention is in particular remarkable because it allows criteria that are difficultly compatible to be reconciled, namely an acquisition by laser scanning in real time with a high sensitivity. Similarly, an adequate miniaturization with a high resolution (large numerical aperture).

BRIEF DESCRIPTION OF THE DRAWINGS

Other advantages and characteristics of the invention will become apparent on examination of the detailed description of an embodiment which is in no way limitative, and the attached drawings, in which.

DETAILED DESCRIPTION OF THE PREFERRED EMBODIMENTS

There will now be described a miniaturized opto-mechanical head provided to equip the distal end of a bundle of flexible optical fibres, intended to be placed in contact with the analysis surface and comprising optical means allowing the focusing of the excitation beam at a given depth beneath the analysis surface and the optimum collection of the fluorescence signal originating from the same volume as the excitation volume (confocal character).

Generally, the opto-mechanical head is constituted:

by a combination of several optics (refractive, diffractive or index-gradient) constituting an achromatic assembly and allowing illumination of the analysis surface while still ensuring a good optical quality necessary to obtain a highly resolved confocal fluorescence image, and by a mechanical assembly allowing:

1. The holding and alignment of the optics with very tight centring and tilt tolerances in order not to deviate from the nominal position, and thus not induce aberrations that may degrade the optical quality and as a result the spatial resolution, and 2. Connection of the opto-mechanical head to the image guide.

This mechanical assembly can be made of a biocompatible metallic material such as for example stainless steel 316L and with minimal thicknesses in order not to block the beams described by the fibres at the edge of the image guide, and not over-increase the dimensions of the optical head. Due to the small space required by the optical head according to the invention, the mechanical items holding the optics present a minimal (less than 300 µm) "skin" thickness (difference between internal diameter and external diameter). Moreover, in order not to degrade the optical quality having a direct impact on sensitivity and spatial resolution, the head is assembled with centring and tilt tolerances of a few microns. This necessitates for example an adjustment of the lenses on an optical bench.

Figure 1:
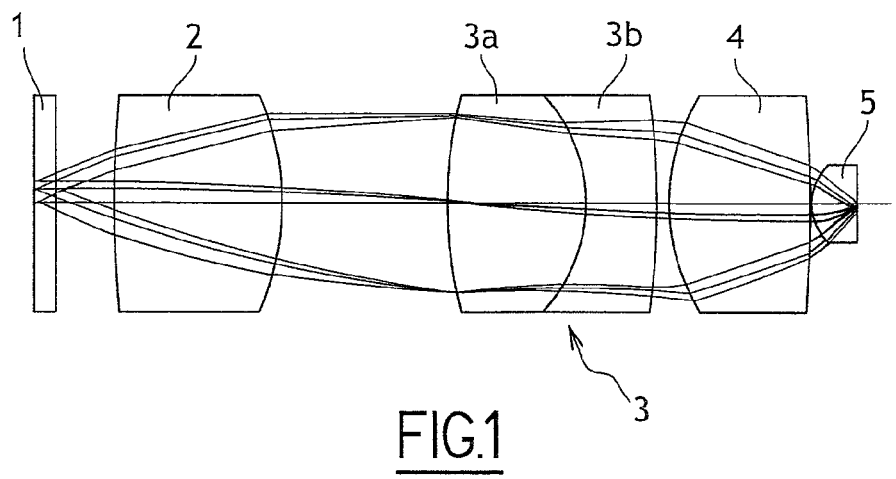
FIG. 1 is a simplified diagram of the optical elements of a miniature head with a magnification of 2.5 according to the invention.
Figure 2:
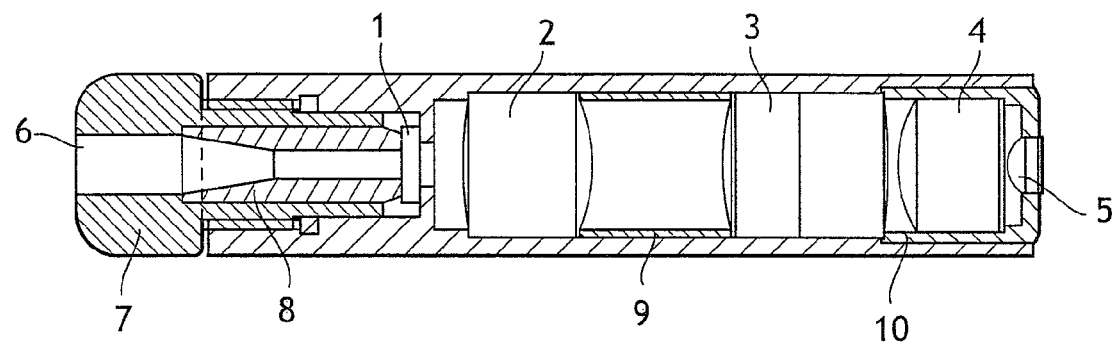
FIG. 2 is a simplified diagram of the opto-mechanical elements of the optical head of FIG. 1.

More precisely, FIG. 1 shows a simplified diagram of an assembly of optical elements of an optical head according to the invention. This device allows a miniature head to be produced as represented in FIG. 2 with a magnification of 2.5.

In FIG. 1, the optical assembly is constituted by a focusing set constituted by a doublet 3, a convergent lens 4 and a hemispherical convergent lens 5. It also comprises an upstream corrective lens represented by the convergent lens 2. The role of the focusing optical set is to focus the excitation beam into an excitation focal point situated in a sub-surface analysis plane. By way of example, this optical set with a magnification equal to 2.5, i.e. a tissue-side numerical aperture of 0.8, is constituted by the achromatic doublet 3 of N-LAK21 and N-SF6 glass, by the bi-convex lens 4 of SK16 glass, and by the hemispherical lens 5 of BK7 glass allowing a significant focusing and a good contact with the analysis surface to be ensured.

In this example, the corrective optical set allowing correction of the aberrations induced by the focusing optical set is constituted by the bi-convex lens 2 of SK16 glass. This corrective optical set has at least three functions. The first function is to create a spherical aberration capable of compensating for the spherical aberrations introduced by other lenses placed downstream in the direction of the excitation; this is achieved in particular by using a significant thickness of glass for the lens L2; the advantage of this is that it is not necessary to add a new lens in order to correct the aberrations of the lenses placed downstream. The second function is that the glass of the third lens L2 is determined with a constringence small enough to minimize the necessary chromatic correction power, and with a high enough refractive index to limit the effect of spherical aberration and coma. The third function is to image the pupil of the optical fibres in a pupillary plane that is as close as possible to these optical fibres so as to obtain a small size pupil, therefore a small diameter for the optical head.

Generally, the two optical and correction focusing sets participate at the same time in the focusing and correction of aberrations, but the focusing optical set plays a leading role in the focusing whereas the corrective optical set plays a leading role in the correction of the aberrations. More precisely, the aberration is unaffected in the focusing optical set and an optical correction set is produced in which the aberration is calculated so as to correct the aberration of the focusing optical set.

The choice of the glasses of the optical system is made so as to make the system achromatic over a broad spectral band [488 nm; 700 nm] and thus make it compatible with use in fluorescence imaging.

The role of a plate 1 with plane and parallel faces made of BK7, or K10 glass, is to eliminate the stray reflection occurring at the output of the image guide (item 6 in FIG. 2) by producing an index matching between the index of the cores constituting the image guide and the index of the glass BK7, and shifting the glass-air reflection into an extra-focal plane. Moreover, the choice of the position (extra-focal plane), of the curve and of an optimum antireflection treatment allows minimization of the stray reflections that may come from the other lenses. This allows the useful signal from the analysis sample not to be interfered with when this miniature head is used within the framework of reflectance imaging.

FIG. 1 shows diagrammatically the optical path length of excitation beams originating from the image guide, one centred on the optical axis of the system, the other two emerging from the optical fibre in the middle then at the field edge with respect to the optical axis of the system.

The beam emerging from the head converges into an excitation focal point situated in a sub-surface analysis plane. The fluorescence (or reflectance) signal re-emitted by the sample takes the same optical path in the opposite direction before being principally re-coupled in the optical illumination fibre.

The detailed characteristics (radius of curvature, thickness, alignment tolerances etc.) of the different lenses as well as the plate of this first embodiment are given in Table I below:

This embodiment allows a very good optical quality to be obtained and thus a high spatial resolution and high sensitivity. Its performances are as follows:

Magnification=2.5

Image numerical aperture=0.8 in water

Image quality very close to the diffraction limit. The wave front error (WFE) is $\lambda/15$ in the centre of the field and $\lambda/10$ at the edge of the field over the whole range of wavelengths between 488 nm and 700 nm. This very good image quality ensures a good return coupling rate in the excitation fibre (90%).

Circled energy: allows the lateral resolution that can be expected to be assessed. In the present case, 50% of the energy originating from the object point is contained in a diameter of 0.5 μm in the centre of the field, and of 1 μm at the edge of the field. In this case, it is not the optical head which limits the lateral resolution, but the distance between the cores of the fibres constituting the image guide. The lateral resolution is given by the inter-core distance divided by the magnification of the optical head, i.e. a lateral optical resolution of 1.3 μm.

Axial resolution: comprised between 3 and 5 μm

Axial chromatism: 2 μm between [488 nm; 700 nm]. This is less than the axial resolution, thus engendering a minimal loss of fluorescence flux.

Lateral chromatism: <0.5 μm between [488 nm; 700 nm]. This is less than the distance between two fibres divided by the magnification, therefore the fibre used for excitation is the same as the collection fibre.

Frontal area: this is the distance between the last optical diopter and the focusing point, which corresponds to the observation distance in the tissue, since the last lens of which the surface is plane is placed in contact with the analysis surface. In the embodiment, this equals 30 μm+/−10 μm. Different frontal area values can be obtained by modifying only the thickness of the last lens L5, the optical head retaining its performance values. Starting from the embodiment detailed in Table 1, an increase of 10 μm in the frontal area is obtained in exchange for a decrease of approximately 10 μm in the geometric thickness of the lens L5.

TABLE 1

| Element | diameter (mm) Nominal | diameter (mm) Useful | Tolerance on lens +/− | thickness (mm) Nominal | thickness (mm) Tol +/− | radius (mm) Nominal | number of fringes | Tol +/− (mm) | glass | Decentration (mm) Tol +/− | Tilt (°) Tol +/− |
|---|---|---|---|---|---|---|---|---|---|---|---|
| Element 1 | 1.80 | 0.65 | — | 0.500 | 0.020 | Inf | | | BK7 | 0.100 | 0.35 |
| Air 1 | | | | 1.200 | 0.010 | Inf | | | | | |
| Element 2 | 3.40 | 2.83 | — | 3.600 | 0.020 | 13.277 | 2.000 | 0.060 | SK16 | 0.016 | 0.20 |
| Air 2 | | | | 3.592 | 0.020 | −3.235 | 2.000 | 0.004 | | | |
| Element 3a | 3.40 | 2.88 | — | 3.000 | 0.020 | 5.424 | 2.000 | 0.010 | N-LAK21 | 0.016 | 0.20 |
| Element 3b | 3.40 | 3.04 | — | 1.500 | 0.020 | −2.016 | 2.000 | 0.001 | N-SF6 | | |
| Air 3 | | | | 0.254 | 0.020 | −10.972 | 2.000 | 0.041 | | | |
| Element 4 | 3.40 | 3.04 | — | 2.977 | 0.010 | 2.554 | 2.000 | 0.002 | SK16 | 0.0215 | 0.50 |
| Air 4 | | | | 0.050 | 0.005 | −17.810 | 2.000 | 0.107 | | | |
| Element 5 | 1.30 | 1.25 | — | 0.948 | 0.005 | 0.677 | 2.000 | 0.001 | BK7 | 0.015 | 0.40 |
| | | | | | | Inf | | | | | |

Notes:
(1) surface irregularity = +/−0.2 lambda
(2) Tolerance of tolerance index = +/−1.10$^{-3}$
(3) Abbe number tolerances = +/−0.5

Field of view: the field of view is defined as the total useful diameter of the image guide divided by the magnification of the optical system, i.e. in this case a field of view of diameter 240 μm.

Transmission: this is of the order of 95% thanks to the use of an optimum antireflection treatment over the band [488 nm; 700 nm].

The optical means of FIG. 1 are to be integrated in an optics-holder tube, forming an optical head, as illustrated in FIG. 2. The mechanical assembly represented in FIG. 2 is constituted by:

a metal tube 4.2 mm in diameter and 22.7 mm long having a first shoulder in which the image guide 6 is inserted with a silica ferrule 8 at its end, and a second shoulder in which the optical elements 2 and 3 are inserted. The tolerance H6 (−0, +8 μm) on the internal diameter of the tube allows a centring and a tilt of the optical element 3 to be achieved that is compatible with the specifications given in Table 1 above.

a mechanical crosspiece of which the tolerance on the external diameter of (−4, −9 μm), the coaxiality and the perpendicularity of 5 μm allows the centring and the tilt positioning of the optical element 2 to be ensured.

a mechanical piece 10 which allows alignment of the lenses 4 and 5 with the remainder of the optical assembly. The tolerance H6 (−0, +8 μm) on the internal diameter and g5 (−4, −9 μm) on the external diameter of the tube allows the centring of the lens 4 which is supported on the shoulder and is then fixed by bonding to be ensured. In order to respect the alignment tilt tolerances of the lens 5, the latter is adjusted on a bench by autocollimation on its plane face.

a metal support 7, the thread of which is identical to that produced in the interior of the tube on the image guide, allows the assembly of the image guide equipped with a silica ferule 8 with the opto-mechanical head. All these mechanical pieces are made of stainless steel 316L (biocompatible material).

The dimensions of the opto-mechanical head presented in this example are 4.2 mm in diameter and 27 mm in length of the rigid part, which presents a sufficient miniaturization for easy manipulation and minimal invasiveness, even none in the case of an imaging by contact with the analysis surface.

Figure 3:
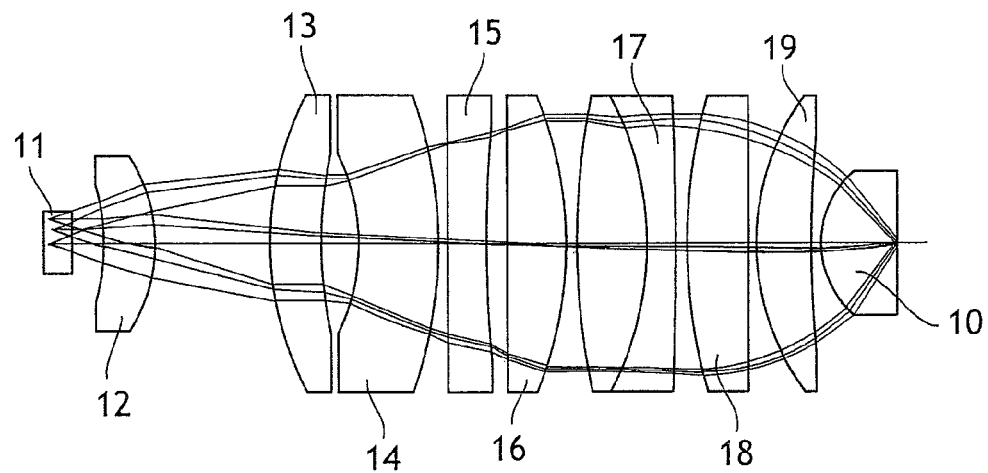
FIG. 3 is a simplified diagram of the optical elements of a miniature head with a magnification of 4 according to the invention.

In FIG. 3, an optical diagram of a miniature head, with a magnification of 4, is shown.

This second embodiment, which has smaller dimensions than the first example, has the advantage that it can be used in vivo by insertion into the operating channel of an endoscope. Moreover, the magnification of 4 (i.e. a numerical aperture of 1.2 in water) allows the following to be obtained:

a better spatial resolution (lateral and axial) of the order of 1 μm, a better sensitivity linked with a larger image numerical aperture (numerical aperture of 1.2 in water).

This solution is more complex, since it operates at a larger numerical aperture while requiring less space, which, a priori, is contrary to use with a large numerical aperture. The use of a large number of lenses allows the required performance values to be achieved while progressively bringing the beam into the focusing set in order to give it the good numerical aperture illumination.

The optical head represented in FIG. 3 is constituted by an optical assembly of nine lenses and a plate 11 with plane and parallel faces. This optical assembly is split into two sets:

the focusing set is constituted by an achromatic doublet 17 of BK7 and SF6 glass, by a piano-convex lens of BK7 glass, by a bi-convex lens 19 of BK7 and by a hemispherical lens 10 of BK7 glass allowing a significant focusing and a good contact with the analysis surface to be obtained.

the corrective optical set allowing correction of the aberrations induced by the focusing optical set is constituted by a biconcave lens 12 of SF6, by a bi-convex lens 13 of BK7 glass, by a bi-concave lens 14 of SF6 glass, by a piano-concave lens 15 of SF6, and by a piano-concave lens 16 of BK7. This corrective optical set is much more complex, since the head has a very large numerical aperture, a single field of view and requires a yet smaller space.

The choice of the glasses of the optical system is made so as to make the system achromatic over a broad spectral band [488 nm; 700 nm] and thus make it compatible with use in fluorescence imaging.

In the same way as for the previous example, the role of the plate with plane and parallel faces made of BK7 is to eliminate the stray reflection present at the output of the image guide, by producing an index matching between the index of the cores constituting the image guide and the index of the BK7, and shifting the glass-air reflection into an extra-focal plane. Moreover, the choice of the position (extra-focal plane), of the curve and of an optimum antireflection treatment allows minimization of the stray reflections that may come from the other lenses. This allows the useful signal originating from the analysis sample not to be interfered with when this miniature head is used within the framework of reflectance imaging.

FIG. 3 shows diagrammatically the optical path length of excitation beams originating from the image guide, one centred on the optical axis of the system, the other two emerging from the optical fibre in the middle and at the edge of the field with respect to the optical axis of the system.

The beam emerging from the plate converges into an excitation focal point situated in a subsurface analysis plane. The fluorescence (or reflectance) signal re-emitted by the sample takes the same optical path in the opposite direction before being principally re-coupled in the optical illumination fibre.

The detailed characteristics (radius of curvature, thickness etc.) of the different lenses as well as of the plate of this second embodiment are given in Table 2 below.

This embodiment allows a very good optical quality to be obtained and thus a high spatial resolution and high sensitivity. Its performances are as follows:

Magnification=4

Image numerical aperture=1.2 in water

Image quality very close to the diffraction limit. The wave front error (WFE) is $\lambda/30$ in the centre of the field and $\lambda/15$ at the edge of the field over the whole range of wavelengths between 488 nm and 700 nm. This very good image quality ensures a return coupling rate in the excitation fibre of more than 90%.

Circled energy: in this example, 50% of the energy originating from the object point is contained in a diameter of 0.34 μm in the centre of the field, and of 0.52 μm at the edge of the field.

Axial resolution: of the order of 2 μm

Axial chromatism: 1.2 μm between [488 nm; 700 nm]. This is less than the axial resolution, thus engendering a minimal loss of fluorescence flux.

Lateral chromatism: 0.1 μm.

Frontal area: this equals 30 μm+/−10 μm. As in the previous embodiment, this embodiment uses an optical head with a fixed frontal area or observation distance.

Field of view: in this case it has a diameter of 150 μm.

Transmission: taking the number of lenses into account, it is of the order of 80% thanks to the use of an optimum antireflection treatment over the band [488 nm; 700 nm].

Optical diameter: 2 mm.

Optical length: 8.6 mm.

These dimensions make this solution compatible with the dimensions of the majority of operating channels of endoscopes.

TABLE 2

| Element | diameter (mm) | thickness (mm) | radius (mm) | glass |
|---|---|---|---|---|
| Element 1 | 1.8 | 0.300 | Inf | BK7 |
| Air 1 | | 0.300 | Inf | |
| Element 2 | 1.2 | 0.500 | −1.031 | SF6 |
| Air 2 | | 1.190 | −0.838 | |
| Element 3 | 2.0 | 0.500 | 1.569 | BK7 |
| Air 3 | | 0.391 | 2.000 | |
| Element 4 | 2.0 | 0.800 | −1.000 | SF6 |
| Air 4 | | 0.100 | −2.128 | |
| Element 5 | 2.0 | 0.390 | Inf | SF6 |
| Air 5 | | 0.223 | 8.006 | |
| Element 6 | 2.0 | 0.600 | Inf | BK7 |
| Air 6 | | 0.100 | −1.776 | |
| Element 7a | 2.0 | 0.700 | 3.176 | BK7 |
| Element 7b | 2.0 | 0.300 | −1.535 | SF6 |
| Air 7 | | 0.100 | −11.055 | |
| Element 8 | 2.0 | 0.600 | 2.338 | BK7 |
| Air 8 | | 0.100 | Inf | |
| Element 9 | 2.0 | 0.550 | 1.258 | BK7 |
| Air 9 | | 0.100 | 6.802 | |
| Element 10 | 2.0 | 0.745 | 0.500 | BK7 |
| | | 0.030 | Inf | |

The optical head according to the invention provides a chromatism correction which allows optimization of the sensitivity along two axes:

1. Correction of the Lateral Chromatism

This correction is necessary in order that the fluorescence signal is coupled on return in the optical fibre that served to illuminate the sample, and not in an adjacent fibre which is spatially filtered through the filtering hole located in front of the detector of the device to which the probe will be connected. Because of this, the lateral chromatism is less than the inter-core distance divided by the magnification of the optical head.

2. Correction of the Axial Chromatism

The presence of axial chromatism in the optical head would manifest itself directly in a loss of sensitivity by return coupling in the optical illumination fibre, since the fluorescence photons would originate from a position Z which would be different from the position Z of the illumination beam, and will thus be filtered by the illumination fibre. In order to avoid this loss of sensitivity, the axial chromatism is less than the axial resolution.

The optical head also allows an optimum transmission and a minimization of stray reflections. The high sensitivity of the optical head also involves the optimization of the outward transmission at the excitation wavelengths and the return transmission at the fluorescence wavelengths, which is all the more important for solutions using complex optical solutions constituted by several lenses. To this end, each lens has an optimum antireflection treatment (R<0.5%) at the operating wavelengths. Moreover, each lens is placed in an extra-focal plane and has a curvature which allows elimination of the signal reflected at excitation length outside the excitation fibre. The coupling rate of the signal reflected by the lenses is less than $10^{-5}$ with respect to the fibre output signal in order to prevent the signal from the observed sample being interfered with by the reflected signal. This last point is necessary above all within the framework of reflectance imaging.

Regarding miniaturization, the requirements in terms of dimensions vary according to the field of application. A distinction is drawn between two cases:

1. Ex-vivo or in-vivo cell imaging in small animals or in people requiring imaging by contact or with reduced invasiveness (laparoscopy etc.) This requirement nevertheless necessitates minimum dimensioning (less than the dimensions of a microscope lens) for reasons of ease of manipulation, namely a diameter less than 5 mm and a length of the rigid part of the head less than 27 mm.

2. In-vivo imaging in small animals or in people by the endoscopic route. This requirement requires dimensions compatible with the dimensions of the operating channel of the endoscope in which the probe will be inserted. A probe measuring less than 2.8 mm in diameter and 15 mm in length of the rigid part is compatible with the majority of the operating channels of endoscopes (gastroscope, colonoscope, etc.).

Generally, the probes produced according to the present invention have numerous qualities:

High Sensitivity:

These probes can operate at depth while still ensuring a very good collection of the fluorescence signal. In fact, due to their very high sample-side numerical aperture and an assembly of optics correcting aberrations, these probes allow excitation of the sample with a significant energy density and they also allow collection of the maximum of fluorescence photons on return.

High Spatial Resolution:

The optical magnification and the presence of an assembly of optics correcting the aberrations in the centre and at the edge of the field allow the illumination of the tissues with a PSF ("point spread function") in the micron range.

A large image numerical aperture combined with the use of optics correcting the spherical aberration allows the illumination of the sample with a planigraphic plane a few microns thick, which gives the probes a very good axial resolution of the image (confocal planigraphic plane capacity). These novel probes therefore have a much better axial resolution, less than 5 µm, unlike the Grins probes for example which reach values of 15 to 20 µm.

Achromatic:

The chromatism problems inherent in fluorescence operations are totally taken into account through the use of specific glasses. The probes based on Grins lenses which constitute the technological basis of several of those involved in the field do not allow correction of these chromatism effects, which means losses of sensitivity, since the excitation plane and fluorescence emission plane are spatially shifted, which then manifests itself in a loss of coupling on return in the optical fibre.

Miniature: These probes have a design compatible with a significant miniaturization, necessary for in-vivo applications and in particular for insertion in the operating channel of an endoscope.

Of course, the invention is not limited to the examples which have just been described and numerous adjustments can be made to these examples without exceeding the scope of the invention.

The invention claimed is:

1. A miniaturized optical head provided to equip the distal end of a bundle of flexible optical fibres scanned by a laser beam, said optical head being configured to come into contact with a sample and to excite said sample in a confocal manner the optical head comprising:

means for correcting spherical aberrations; and
   focusing means,
   wherein the focusing means comprises at least a first strongly convergent lens combined with a spherical or hemispherical lens arranged at the distal end of the optical head, and
   means for correcting axial and lateral chromatism that are provided with a single divergent lens the curvature of which is substantially centered on the pupil of the bundle of optical fibres and arranged at the correct distance from this pupil for which the lateral achromatization conditions coincide with the axial achromatization conditions, the divergent lens being combined with a second convergent lens in the form of a doublet,
   wherein the means for correcting spherical aberrations comprise a third convergent lens, the thicknesses of the first and third convergent lenses being determined so as to correct the cumulative spherical aberration on the convergent diopters, and
   wherein the thickness of the third convergent lens is also determined so as to image the pupil on the second convergent lens.

2. The optical head according to claim 1, wherein the means for correcting spherical aberrations comprise a third convergent lens, the thickness, the radius of curvature and the nature of this third lens being adapted so as to image the pupil in a plane situated as close as possible to said bundle of optical fibres.

3. The optical head according to claim 1, wherein a glass of the third lens is determined with a small enough constringence to minimize the necessary chromatic correction power, and with a large enough refractive index to limit the spherical and coma aberration effect.

4. The optical head according to claim 1, wherein said doublet is placed in a pupillary plane.

5. The optical head according to claim 1, wherein said doublet is constructed of glass and comprises a pair of glasses having an index difference and a chromatic dispersion difference so as to compensate for the chromatic aberrations of the convergent lenses.

6. The optical head according to claim 1, wherein the divergent lens is curved so as to obtain a numerical aperture greater than 0.8.

7. The optical head according to claim 1, wherein the first and third convergent lenses are each obtained from a lens having a first radius and a second radius larger than the first radius, said second radius being made plane so as to obtain a plano-convex lens.

8. The optical head according to claim 1, wherein the first convergent lens is designed and arranged so as to eliminate the image of the pupil sufficiently far ahead to minimize the astigmatism generated by the spherical or hemispherical lens (L5) in the imaged field.

9. The optical head according to claim 1, wherein the hemispherical lens is produced in a ball, the plane output face of which is obtained by abrasion on a plane polisher.

10. The optical head according to claim 1, wherein the thickness of the hemispherical lens is adjusted in order to obtain a predetermined frontal area of the optical head.

11. The optical head according to claim 10, wherein the axial position of the hemispherical lens is determined according to the thickness of said hemispherical lens in order to optimize the optical performances of the optical head for said frontal area.

12. The optical head according to claim 1, further comprising:
   a plate with plane faces for eliminating the stray reflection occurring at the output of the bundle of optical fibres.

13. The optical head according to claim 1, wherein a signal collected by the optical head that originates from the sample is a fluorescence signal.

14. The optical head according to claim 1, wherein a signal collected by the optical head that originates from the sample is a reflectance signal.

15. The optical head according to claim 1, wherein the bundle of optical fibres is scanned by the laser beam in real time so as to acquire at least twelve images per second.

16. A miniaturized optical head provided to equip the distal end of a bundle of flexible optical fibres scanned by a laser beam, said optical head being configured to come into contact with a sample and to excite said sample in a confocal manner the optical head comprising:

means for correcting spherical aberrations; and
   focusing means,
   wherein the focusing means comprises
      at least a first strongly convergent lens combined with a spherical or hemispherical lens arranged at the distal end of the optical head, and
      means for correcting axial and lateral chromatism that are provided with a single divergent lens the curvature of which is substantially centered on the pupil of the bundle of optical fibres and arranged at the correct distance from this pupil for which the lateral achromatization conditions coincide with the axial achromatization conditions, the divergent lens being combined with a second convergent lens in the form of a doublet,
   wherein the means for correcting spherical aberrations comprise a third convergent lens, the thicknesses of the first and third convergent lenses being determined so as to correct the cumulative spherical aberration on the convergent diopters.

17. A miniaturized optical head provided to equip the distal end of a bundle of flexible optical fibres scanned by a laser beam, said optical head being configured to come into contact with a sample and to excite said sample in a confocal manner the optical head comprising:

means for correcting spherical aberrations; and
   focusing means,
   wherein the focusing means comprises
   at least a first strongly convergent lens combined with a spherical or hemispherical lens arranged at the distal end of the optical head, and
   means for correcting axial and lateral chromatism that are provided with a single divergent lens the curvature of which is substantially centered on the pupil of the bundle of optical fibres and arranged at the correct distance from this pupil for which the lateral achromatization conditions coincide with the axial achromatization conditions, the divergent lens being combined with a second convergent lens in the form of a doublet,
   wherein said doublet is constructed of glass and comprises a pair of glasses having an index difference and a chromatic dispersion difference so as to compensate for the chromatic aberrations of the convergent lenses.

* * * * *